(12) United States Patent
Borza et al.

(10) Patent No.: US 8,008,326 B2
(45) Date of Patent: Aug. 30, 2011

(54) 4-BENZYLEDENE-PIPERIDIN DERIVATIVES

(75) Inventors: Istvan Borza, Budapest (HU); Csilla Horvath, Budapest (HU); Sandor Farkas, Budapest (HU); Istvan Gyertyan, Budapest (HU); Jozsef Nagy, Budapest (HU); Sandor Kolok, Budapest (HU); Kornel Galgoczy, Budapest (HU); Katalin Saghy, Budapest (HU)

(73) Assignee: Richter Gedeon Vegyeszeti Gyar Rt., Budapest (HU)

( * ) Notice: Subject to any disclaimer, the term of this patent is extended or adjusted under 35 U.S.C. 154(b) by 1209 days.

(21) Appl. No.: 11/658,789

(22) PCT Filed: Jul. 21, 2005

(86) PCT No.: PCT/HU2005/000077
§ 371 (c)(1),
(2), (4) Date: Jan. 25, 2007

(87) PCT Pub. No.: WO2006/010964
PCT Pub. Date: Feb. 2, 2006

(65) Prior Publication Data
US 2008/0312222 A1    Dec. 18, 2008

(30) Foreign Application Priority Data
Jul. 29, 2004 (HU) .................... 0401522

(51) Int. Cl.
*A61K 31/445* (2006.01)
*C07D 401/12* (2006.01)
*C07D 413/12* (2006.01)
*C07D 417/12* (2006.01)

(52) U.S. Cl. ........ 514/321; 514/322; 514/323; 546/198; 546/199; 546/200; 546/201

(58) Field of Classification Search .................. 514/321, 514/322, 323; 546/198, 199, 200, 201
See application file for complete search history.

(56) References Cited

U.S. PATENT DOCUMENTS
6,359,138 B1    3/2002  Alanine et al. ................. 546/201
2004/0157886 A1  8/2004  Domany et al. ................ 514/317

OTHER PUBLICATIONS

Kornberg et al. "Subtype selectvie NMDA . . . " Bioorg. Med. Chem. Lett. v. 14, p. 1213-1216 (2004).*

* cited by examiner

*Primary Examiner* — Celia Chang
(74) *Attorney, Agent, or Firm* — Fish & Richardson P.C.

(57) ABSTRACT

The present invention relates to new 4-benzylidene-piperidin derivatives of formula (I), useful as NMDA, in a particular NR2B subunit containing receptor antagonists and analgesica.

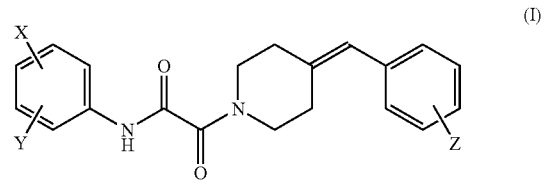

8 Claims, No Drawings

US 8,008,326 B2

4-BENZYLEDENE-PIPERIDIN DERIVATIVES

The invention relates to new 4-benzylidene-piperidine derivatives which are NR2B selective NMDA receptor antagonists with improved in vivo profile or are intermediates for preparing thereof.

BACKGROUND OF THE INVENTION

N-methyl-D-aspartate (NMDA) receptors are ligand-gated cation-channels widely expressed in the central nervous system. NMDA receptors are involved in developmental and plastic changes of neurons. Overactivation of NMDA receptors by glutamate, their natural ligand, can lead to calcium overload of cells. This triggers a cascade of intracellular events that alters the cell function and ultimately may lead to death of neurones. Antagonists of the NMDA receptors may be used for treating many disorders that are accompanied with excess release of glutamate or overactivation of NMDA receptor for any reason [Curr Opin Investig Drugs. 2003 4: 826-32].

The NMDA receptors are heteromeric assemblies built up from at least one NR1 subunit together with one or more of the four NR2 subunits (NR2A-D). Both spatial distributions in the CNS and the pharmacological sensitivity of NMDA receptors built up from various NR2 subunits are different. Particularly interesting of these is the NR2B subunit due to its restricted distribution (highest densities in the forebrain and substantia gelatinosa of the spinal cord) [Neuropharmacology, 38, 611-623 (1999)]. Compounds selective for this subtype are available and have been proved to be effective in animal models of stroke [Stroke, 28, 2244-2251 (1997)], traumatic brain injury [Brain Res., 792, 291-298 (1998)], Parkinson's disease [Exp. Neurol., 163, 239-243 (2000)], neuropathic and inflammatory pain [Neuropharmacology, 38, 611-623 (1999)].

Moreover, NR2B subtype selective antagonists of NMDA receptors may provide therapeutic advantage over non-selective antagonists of NMDA receptors. The channel blocker type non-selective NMDA antagonists phencyclidine and ketamine induce psychotomimetic effects, hallucinations, dysphoria, catatonia and amnesia in man. These serious adverse effects hinder their clinical use as potential medication. Compounds belonging to this class cause behavioural abnormalities in animals, too, e.g. stimulate motor activity, induce, amnesia and impair motor-coordination. The severity of these effects in animals is considered to be predictive for the intensity of clinical side effects. NR2B subtype selective antagonists are expected to lack most of these side effects. In animal behavioural studies some NR2B selective compounds [Ro 63-1908 in J. Pharmacol. Exp. Ther., 302 (2002) 940-948 and Ro 25-6981 in Behav. Pharmacol., 14 (2003) 477-487] were reported to increase locomotor activity while no such effect was observed with CP-101,606, another NR2B selective antagonist, and Ro 256981 by an other group [Neuropharmacology, 38, 611-623 (1999)]. Lack of locomotor stimulating effect of CP-101,606 up to 56 mg/kg s.c. and 100 mg/kg i.p. was confirmed by others [Soc. Neurosc. Abstr. 21, 439.9. 1995.]. Thus, to our best knowledge, CP-101,606 is the only NR2B selective antagonist consistently reported to lack locomotor stimulating effect. Since CP-101,606 appears to have poor oral efficacy and according to published information was investigated only by intravenous route of administration in humans, moreover it has polymorph CYP2D6 mediated metabolism [Drug Metabolism and Disposition 31: 76-87], there remains to be a great need for new NR2B antagonists with low side effect liability (high therapeutic index) good oral efficacy (bioavailability) and good developability for therapeutic purposes, especially for oral treatment.

Saturated analogues of the compounds of the present invention are described in patent No. WO 2003010159 as NR2B subtype selective NMDA antagonists. However, other close structure analogues of the 4-benzylidene-piperidine derivatives of formula (I) are unknown in the literature.

SUMMARY OF THE INVENTION

It was found that the new 4-benzylidene-piperidine derivatives of formula (I) of the present invention are functionally active NMDA antagonists selective for NR2B subunit containing receptors. We also found that benzylidene-piperidines have in vivo analgesic potency similar to that of their saturated benzyl-piperidine analogues. Surprisingly, while the latter molecules cause locomotor stimulation at or slightly above their maximally effective analgesic dose, compounds of the present invention are free from locomotor stimulatory effect up to 40-60-fold analgesic doses. This feature may provide therapeutic advantage over NR2B selective NMDA antagonists with lower therapeutic index.

DETAILED DESCRIPTION OF THE INVENTION

The present invention relates therefore first to new 4-benzylidene-piperidin derivatives of formula (I)

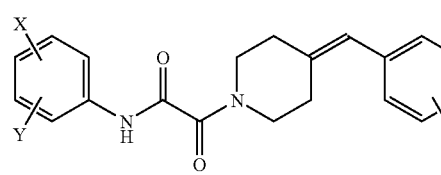

(I)

wherein the meaning of

X and Y independently are hydrogen or halogen atom, hydroxy, cyano, nitro, amino, $C_1$-$C_4$ alkylamino optionally substituted by a halogen atom or halogen atoms, arylamino optionally substituted by a halogen atom or halogen atoms, aralkylamino optionally substituted by a halogen atom or halogen atoms, $C_1$-$C_4$ alkylsulfonamido optionally substituted by a halogen atom or halogen atoms, $C_1$-$C_4$ alkanoylamido optionally substituted by a halogen atom or halogen atoms, arylsulfonamido, $C_1$-$C_4$ alkylsulfonyloxy, carboxyl, trifluoromethyl, trifluoromethoxy, $C_1$-$C_4$ alkyl-$SO_2$—NH—$CH_2$—, $NH_2$—$(CH_2)_{1-4}$—$SO_2$—NH—, $NH_2$—$(CH_2)_{1-4}$—(CO)—NH—, sulfamoyl [$NH_2$—$SO_2$—], formyl [—CHO], amino-methyl [—$CH_2$—$NH_2$], hydroxymethyl, $C_1$-$C_4$ alkyl, $C_1$-$C_4$ alkoxymethyl, halogenmethyl, tetrazolyl group, or $C_1$-$C_4$ alkoxy, $C_1$-$C_4$ alkoxycarbonyl, $C_1$-$C_6$ alkanoyloxy, phenyl or $C_1$-$C_4$ alkoxy groups, optionally substituted by amino group, or the neighboring X and Y groups in given case together with one or more identical or different additional hetero atom and —CH= and/or —$CH_2$— groups can form an optionally substituted 4-7 membered homo- or heterocyclic ring, preferably morpholine, pyrrole, pyrrolidine, oxo- or thioxo-pyrrolidine, pyrazole, pyrazolidine, imidazole, imidazolidine, oxo- or thioxo-imidazole or imidazolidine, 1,4-oxazine, oxazole, oxazolidine, oxo- or thioxo-oxazolidine, oxo- or thioxo-thiazolidine or 3-oxo-1,4-oxazine ring, Z is hydrogen or halogen atom, nitro, amino, $C_1$-$C_4$ alkyl, $C_1$-$C_4$ alkoxy, cyano, trifluoromethyl, trifluoromethoxy group— and optical antipodes, racemates and salts thereof.

Furthermore objects of the present invention are the pharmaceutical compositions containing new 4-benzylidene-piperidin derivatives of formula (I) or optical antipodes or racemates or the salts thereof as active ingredients.

Further objects of the invention are the processes for producing new 4-benzylidene-piperidin derivatives of formula (I), and the pharmaceutical manufacture of medicaments containing these compounds, as well as the process of treatments with these compounds, which means administering to a mammal to be treated—including human—effective amount/amounts of new benzylidene piperidine derivatives of formula (I) of the present invention as such or as medicament.

According to the invention the carboxylic acid amide compounds of formula (I) can be prepared by the following process.

For producing compound of formula (I), where X, Y and Z are as defined for formula (I), a secondary amine of formula (II)

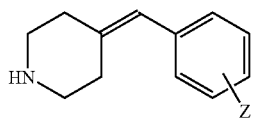
(II)

where Z has the same meaning as given for formula (I)—is reacted with ethyl oxalylchloride in a suitable solvent in the presence of a base,
the obtained ester compound of formula (III)

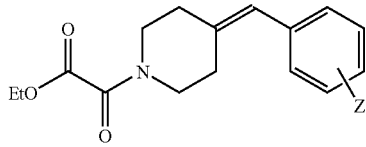
(III)

where Z has the same meaning as given for formula (I)—is saponified with an alkali hydroxide and
the obtained oxalamid acid of formula (IV)

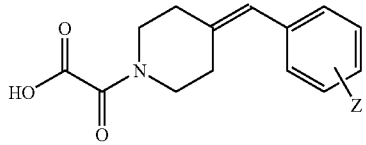
(IV)

wherein the meaning of Z is as described above for formula (I)—or a reactive derivative of it is reacted with an aniline of formula (V)

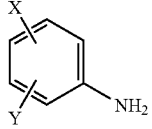
(V)

wherein the meaning of X and Y are as given before for formula (I)—, then the obtained 4-benzylidene-piperidin derivatives of formula (I)—wherein the meaning of X, Y, Z are as defined for formula (I)—in given case are transformed into another compounds of formula (I) by introducing new substituents and/or modifying or removing the existing ones, and/or by forming salt and/or by liberating the compound from salts, and/or by resolving the obtained racemates using optically active acids or bases by known methods.

The reaction of the carboxylic acid of formula (II) and the aniline, of formula (V), i.e. the amide bond formation is preferably carried out by preparing an active derivative from the carboxylic acid of formula (II) and this is reacted with the aniline of formula (V) preferably in the presence of a base.

The transformation of a carboxylic acid into an active derivative is carried out in situ during the amide bond formation in a solvent (for example dimethylformamide, acetonitrile, chlorinated hydrocarbons or hydrocarbons). The active derivatives can be acid chlorides (for example prepared from carboxylic acid with thionyl chloride), mixed anhydrides (for example prepared from carboxylic acid with isobutyl chloroformate in the presence of a base, e.g. triethylamine), active esters (for example prepared from carboxylic acid with hydroxybenztriazol and dicyclohexyl-carbodiimide or O-benzotriazol-1-yl-N,N,N',N'-tetramethylizronium hexafluorophosphate (BBTU) in the presence of a base e.g. triethylamine). The active derivatives are prepared between room temperature and 0° C. The necessary reaction time is 6-20 h. The reaction mixture is purified by column chromatography using Kieselgel 60 (Merck) as adsorbent and a proper eluent. The proper fractions are concentrated to give the pure product. The quality and the quantity of the product are determined by HPLC-MS method.

The anilines of formula (V) are either commercially available or can be synthesized by different known methods. The syntheses of some commercially not available anilines of formula (V) and the carboxylic acids of formula (IV) are described in the Examples.

As said, the new 4-benzylidene-piperidin derivatives of formula (I) of the present invention are highly effective and selective antagonists of NMDA receptor, and moreover most of the compounds are selective antagonist of NR2B subtype of NMDA receptor. For characterization of the NR2B selective NMDA antagonist potency of the compounds we used cultured cortical neurones expressing predominantly NR2B subunit containing NMDA receptors. To prove their selectivity HEK-293 cells transfected with NR1/NR2A subunit combinations were used. To measure the in vivo analgesic potency and side effect liability of potent NR2B selective antagonists we used the mouse formalin and locomotor activity tests, respectively.

Experimental Protocols
Expression of Recombinant NMDA Receptors

To prove NR2B selectivity of the compounds, that is to investigate their effect on NR2A containing NMDA receptors, we tested the most potent ones on cell lines stably expressing recombinant NMDA receptors with subunit compositions of NR1/NR2A. cDNAs of human NR1 and NR2A subunits subcloned into inducible mammalian expression vectors were introduced into HYK 293 cells lacking NMDA receptors using a cationic lipid-mediated transfection method [Biotechniques, 22, 982-987. (1997); Neurochemistry International, 43, 19-29. (2003)]. Resistance to neomycin and hygromycin was used to screen for clones possessing both vectors and monoclonal cell lines were established from the clones producing the highest response to NMDA exposure. Compounds were tested for their inhibitory action on NMDA evoked cytosolic calcium elevations in fluorescent calcium measurements. Studies were performed 48-72 h after addition of the inducing agent. Ketamine (500 μM) was also present during the induction in order to prevent cytotoxicity.
Assessment of NMDA Antagonist Potency In Vitro by Measurement of Intracellular Calcium Concentration with a Plate Reader Fluorimeter in Rat Cortical Cell Culture The intracellular calcium measurements were carried out on primary neocortical cell cultures derived from 17 day old Charles River rat embryos (for the details on the preparation of neocortical cell culture see Johnson, M. I.; Bunge, R. P. (1992): Primary cell cultures of peripheral and central neurons and glia. In: Protocols for Neural Cell Culture, eds: Fedoroff, S.; Richardson A., The Humana Press Inc., 51-75.) After isolation the cells were plated onto standard 96-well microplates and the cultures were maintained in an atmosphere of 95% air-5% $CO_2$ at 37° C. until the calcium measurements.

The cultures were used for the intracellular calcium measurements after 3-7 days in vitro. The cells at this in vitro age are believed to express predominantly NR2B containing NMDA receptors [Mol. Pharmacol. 45, 846-853. (1994)]. Before the measurement the cells were loaded with a fluorescent $Ca^{2+}$-sensitive dye, Fluo-4/AM (2 μM). To stop loading the cells were washed twice with the solution used for the measurement (140 mM NaCl, 5 mM KCl, 2 mM $CaCl_2$, 5 mM HEPES, 5 mM HEPES-Na, 20 mM glucose, 10 μM glycine, pH=7.4). After washing, the test compounds were added to the cells in the above solution (90 μl well). Intracellular calcium measurements were carried out with a plate reader fluorimeter: elevation of Fluo-4-fluorescence and so, intracellular calcium concentration was induced by application of 40 μM NMDA. Inhibitory potency of the test compounds was assessed by measuring the reduction in the calcium elevation in the presence of different concentrations of the compounds.

Dose-response curves and $IC_{50}$-values were calculated using data derived from at least three independent experiments. Inhibitory potency of a compound at a single concentration point was expressed as percent inhibition of the NMDA response. Sigmoidal concentration-inhibition curves were fit to the data and $IC_{50}$ values were determined as the concentration that produces half of the maximal inhibition caused by the compound.

In Table 1, NR2B antagonist potencies of the most effective compounds of this invention determined in this test are listed. The results with several known selective NR2B antagonist reference compounds and the non-selective NMDA receptor antagonist MK-801 are given in Table 2.

TABLE 1

NMDA antagonist activity of compounds measured by fluorimetric method on cortical cells (NR2B activity) or on transfected HEK293 cells (NR2A activity).

| Compound of Table 5 | Rat cortical cells (NR2B) appr. $IC_{50}$ | HEK293 cells (NR2A) Inhibition at 15 μM |
|---|---|---|
| 3 | ++ | — |
| 5 | +++ | N.E. |
| 6 | ++ | — |
| 7 | + | — |
| 10 | ++ | — |
| 11 | +++ | — |
| 12 | +++ | — |
| 13 | ++ | — |
| 14 | ++ | — |
| 15 | +++ | — |

TABLE 1-continued

NMDA antagonist activity of compounds measured by fluorimetric method on cortical cells (NR2B activity) or on transfected HEK293 cells (NR2A activity).

| Compound of Table 5 | Rat cortical cells (NR2B) appr. $IC_{50}$ | HEK293 cells (NR2A) Inhibition at 15 μM |
|---|---|---|
| 16 | ++ | — |
| 17 | + | — |
| 20 | ++ | — |
| 22 | +++ | N.E. |
| 23 | ++ | — |
| 25 | +++ | — |
| 26 | ++ | — |
| 27 | ++ | — |
| 30 | ++ | — |
| 32 | +++ | N.E. |
| 33 | ++ | — |
| 35 | +++ | — |
| 40 | +++ | N.E. |
| 41 | +++ | N.E. |
| 42 | + | — |
| 1 | +++ | N.E. |

+: IC50 is between 500 and 1000 nM
++: IC50 is between 50 and 500 nM
+++: IC50 is less than 50 nM
—: not tested
N.E.: not effective, i.e. inhibition less than 30%

TABLE 2

NMDA antagonist activity of reference compounds measured by fluorimetric method on cortical cells (NR2B activity) or on transfected HEK293 cells (NR2A activity).

| Code of reference compound | rat cortical cells | | NR1-3/NR2A | |
|---|---|---|---|---|
| | $IC_{50}$ [nM] | n | % inhibition at 10 μM | n |
| CI-1041 | 6.6 | 4 | 21.0 | 1 |
| Co-101244 | 23 | 3 | −8.7 | 1 |
| EMD 95885 | 35 | 1 | 0.1 | 1 |
| CP-101,606 | 41 | 3 | 2.5 | 1 |
| Ro 25.6981 | 159 | 4 | 1.0 | 1 |
| Erythro-ifenprodil | 483 | 5 | −2.7 | 1 |
| MK-801 | 37 | 3 | $IC_{50}$ = 386 nM | 2 |

The reference compounds are as follows:
CI-1041: 6-{2-[4-(4-fluoro-benzyl)-piperidin-1-yl]-ethanesulfinyl}-3H-benzooxazol-2-one
Co 101244: 1-[2-(4-hydroxyphenoxy)ethyl]-4-hydroxy-4-(4-methylbenzyl)piperidine
EMD 95885: 6-[3-(4-fluorobenzyl)piperidine-1-yl]propionyl]-2,3-dihydro-benzoxazol-2-on
CP-101,606: (1S,2S)-1-(4-hydroxyphenyl)-2-(4-hydroxy-4-phenylpiperidine-1-yl)-1-propanol
Ro 256981: R—(R*,S*)-1-(4-hydroxyphenyl)-2-methyl-3-[4-(phenylmethyl)piperidine-1-yl]-1-propanol.
Ifenprodil: erythro-2-(4-benzylpiperidino)-1-(4-hydroxyphenyl)-1-propanol
MK-801: (+)-5-Methyl-10,11-dihydro-5H-dibenzo[a,d]cyclohepten-5,10-imine
Mouse Formalin Test for Measurement of In Vivo Efficacy Injection of diluted formalin into the hind paw of rats or mice is known to elicit a biphasic pain-related behaviour measured as time spent by licking/biting of the injured paw. The second phase is generally defined as pain related events detected in the 15-60 min. time interval after formalin injection, with peak activity at around 30 min. It is known that NMDA receptors are involved in the second phase of response to formalin injection and this behavioural response is sensitive to blockade of NMDA receptors [Dickenson, A. and Besson J.-M. (Editors): Chapter 1, pp. 6-7: Animal models of Analgesia; and Chapter 8, pp. 180-183. Mechanism of Central Hypersensitivity: Excitatory Amino Acid Mechanisms and Their Control—In Pharmacology of Pain. Springer-Verlag (Berlin) 1997.] Therefore, we used the second phase of formalin test to characterize the efficacy of compounds in vivo. Inhibition of the second phase of response is considered to indicate an analgesic effect against chemically-induced persistent pain [Hurker, S., et al.: Formalin Test in Mice, a Useful Technique for Evaluating Mild Analgesics, Journal of Neuroscience Methods, 14 (1985) 69-76.]

Male NMRI rice (20-25 g) were used. Prior to the experiment any solid food was withdrawn for approx. 16 hours but the animals had free access to 20% glucose solution. The animals were allowed 1 hour acclimatization period in a glass cylinder (cc. 15 cm in diameter), then moved to an identical cylinder with a mirror placed behind to facilitate observation. The test substances were suspended in 5% tween-80 (10 ml per kg body weight). and administered orally by gavage 15 min before the formalin injection (20 µl of 1% formalin in 0.9& saline injected subcutaneously into the dorsal surface of the right hindpaw). The time spent by licking and biting of the injected paw was measured from 20 to 25 min. after the formalin injection. For the determination of $ED_{50}$ value, various doses (at least five) of the test substances were given to groups of 5 mice and the results expressed as % inhibition of the time spent by licking relative to a vehicle control group observed on the same day. $ED_{50}$ values (i.e. the dose yielding 50% inhibition) were calculated by Boltzman's sigmoidal curve fitting.

Measurement of Spontaneous Locomotor Activity in Mice

Male NMRI mice weighing 20-22 g were used in the experiments.

Spontaneous locomotor activity was measured in a four-channel activity monitor. The apparatus consisted of acrylic cages (43 cm×43 cm×32 cm) equipped with 2×16 pairs of photocells along all the bottom axis of the cage. An additional array of photocells (16 pairs) was placed along two opposite sides of the cage at the height of 10 cm in order to detect rearing responses.

Experimental groups consisted of 10 animals. Thirty minutes after the oral administration of the test compound or vehicle (tween-80), the animals were individually placed in one of four cages for one hour. Horizontal and vertical movements were determined as the number of beam interruptions for one hour at 15 ruin intervals.

Mean±SE of horizontal activity data of each group was calculated then percentual changes compared to the control (vehicle-treated) group were determined. A compound was considered to cause locomotor stimulation when its effect exceeded 50% increase in beam interruptions. Consequently, doses defined as free from stimulatory action ($LMA_{free}$) produced less than 50% increase.

Table 3 shows the results obtained with some selected compounds of the present invention (upper table) and their close benzyl-piperidine analogues (lower table) in the analgesic and locomotor activity tests. [A=2-(4-benzyl-piperidin-1-yl)-2-oxo-N-(2-oxo-2,3-dihydro-benzoxazol-6-yl)-acetamide and B=2-[4-[4-methyl-benzyl)-piperidin-1-yl]-2-oxo-N-(2-oxo-2,3-dihydro-1H-indol-5-yl)-acetamide] Thus, pairs 1-A and 24-B differ only in the presence of double instead of single bound.

TABLE 3

Characterization of the two types of NR2B antagonists in formalin test and locomotor activity (LMA) test. Calculation of therapeutic indices (TI)

berizilidene-piperidines

| Compound of Table 5 | Formalin ED50 mg/kg | LMA dose mg/kg | LMA % increase | TI $LMA_{free}/ED_{50}$ |
|---|---|---|---|---|
| 1 | 1 | 60 | 35* | 46 |
|  |  | 120 | 69 |  |
| 24 | 0.94 | 60 | 13* | >64 | benzyl-piperidines

| Reference compound | Formalin ED50 mg/kg | LMA dose mg/kg | LMA % increase | TI $LMA_{free}/ED_{50}$ |
|---|---|---|---|---|
| A | 0.85 | 1 | 34* | <1.2 |
|  |  | 3 | 62 |  |
| B | 0.48 | 3.75 | 72 | <8 |
|  |  | 7.5 | 141 |  |

*less than 50% is considered as free from side effect

Analgesic and motor activity data for the non-selective NMDA receptor antagonist MK-801 and the selective NR2B antagonists CI-1041 (Soc Neurosci Abst 2000, 26 (Part 2): Abst 527.4.), CP-101,606 and Ro-256981 are given in Table 4.

TABLE 4

Characterization of NMDA antagonist reference compounds in formalin test and locomotor activity (LMA) test. Calculation of therapeutic indices (TI)

reference compounds

| Code of reference compound | Formalin ED50 mg/kg | LMA dose mg/kg | LMA % inc. | TI $LMA_{free}/ED_{50}$ |
|---|---|---|---|---|
| MK-801 | 0.15 | 0.1 | 114 | <1 |
|  |  | 0.3 | 217 |  |
| CI-1041 | 2.4 | 10 | 137 | <4 |
| Ro 25-6981 | >20* |  |  |  |
| CP-101,606 | >20* |  |  |  |

*CP-101,606 and Ro-256981 resulted in only 38% and 12% inhibition of formalin response, respectively, at 20 mg/kg.

It can be seen that the non-selective antagonist of the NMDA receptor, MK-801 increases locomotor activity in the pharmacologically active dose range. This LMA stimulatory effect is an untoward side effect. Certain selective NR2B antagonist compounds like the reference molecule CI-1041 or benzyl-piperidine compounds [A=2-(4-benzyl-piperidin-1-yl)-2-oxo-N-(2-oxo-2,3-dihydro-benzoxazol-6-yl)-acetamide and B=2-[4-[4-methyl-benzyl)-piperidin-1-yl]-2-oxo-N-(2-oxo-2,3-dihydro-1H-indol-5-yl)-acetamide] described in patent application WO 2003010159 also show little separation between the doses causing analgesia and those stimulating locomotor activity. Surprisingly, the benzylidene-piperidine variants of the latter molecules, that is, compounds of the present invention do not cause hyperactivity up to very high doses (Table 3). While TIs of the tested benzylpiperidines with high in vivo potency range from 1 to 8; TIs of their benzylidenpiperidine counterparts are in a considerably higher range, between 46 and 64 or higher. This strikingly different profile was not expected after the seemingly minor structural modification.

NR2B antagonists with large TI may be particularly advantageous for pharmacotherapy of diseases that might be treated with NR2B antagonists. Among benzylidenpiperidines there are compounds with high efficacy in persistent pain model and with high therapeutic index. Compounds of the present invention possess much more favourable profile regarding possible therapeutic use than previously patented compounds.

Disorders which may be beneficially treated with NMDA antagonists acting at NR2B site, as reviewed recently by Loftis [Pharmacology & Therapeutics, 97, 55-85 (2003)] include schizophrenia, Parkinson's disease, Huntington's disease, excitotoxicity evoked by hypoxia and ischemia, seizure disorders, drug abuse, and pain, especially neuropathic, inflammatory and visceral pain of any origin Eur. J. Pharmacol., 429, 71-78 (2001)].

Due to their reduced side effect liability compared to non-selective NMDA antagonists, NR2B selective antagonists may have utility in diseases where NMDA antagonists may be effective, such as amyotrophic lateral sclerosis [Neurol. Res., a 309-12 (1999)], withdrawal syndromes of e.g. alcohol, opioids or cocaine [Drug and Alcohol Depend., 59, 1-15 (2000)], muscular spasms [Neurosci. Lett., 73, 143-148 (1987)], dementia of various origins [Expert Opin. Investig. Drugs, 9, 1397-406 (2000)], anxiety, depression, migraine, hypoglycemia, degenerative disorders of the retina (e.g. CMV retinitis), glaucoma, asthma, tinnitus, hearing loss [Drug News Perspect 11, 523-569 (1998) and WO 00/00197 international patent application].

Accordingly, effective amounts of the compounds of the invention may be beneficially used for the treatment of traumatic injury of brain or spinal cord, tolerance and/or dependence to opioid treatment of pain, withdrawal syndromes of drugs of abuse e.g. alcohol, opioids or cocaine, ischemic CNS disorders, chronic neurodegenerative disorders, such as e.g. Alzheimer's disease, Parkinson's disease, Huntington's disease, pain and chronic pain states, such as e.g. neuropathic pain.

The compounds of the invention as well as their pharmaceutically acceptable salts can be used as such or suitably in the form of pharmaceutical compositions. These compositions (drugs) can be in solid, liquid or semiliquid form and pharmaceutical adjuvant and auxiliary materials can be added, which are commonly used in practice, such as carriers, excipients, diluents, stabilizers, wetting or emulsifying agents, pH- and osmotic pressure-influencing, flavoring or aromatizing, as well as formulation-promoting or formulation-providing additives.

The dosage required to exert the therapeutical effect can vary within broad limits and will be fitted to the individual requirements in each of the particular cases, depending on the stage of the disease, the condition and the bodyweight of the patient to be treated, as well as the sensitivity of the patient against the active ingredient, route of administration and number of daily treatments. The actual dose of the active ingredient to be used can safely be determined by the attending physician skilled in the art in the knowledge of the patient to be treated.

The pharmaceutical compositions containing the active ingredient according to the present invention usually contain 0.01 to 100 mg of active ingredient in a single dosage unit. It is; of course possible that the amount of the active ingredient in some compositions exceeds the upper or lower limits defined above.

The solid forms of the pharmaceutical compositions can be for example tablets, dragées, capsules, pills or lyophilized powder ampoules useful for the preparation of injections. Liquid compositions are the injectable and infusable compositions, fluid medicines, packing fluids and drops. Semiliquid compositions can be ointments, balsams, creams, shaking mixtures and suppositories.

For the sake of a simple administration it is suitable if the pharmaceutical compositions comprise dosage units containing the amount of the active ingredient to be administered once, or a few multiples or a half, third or fourth part thereof. Such dosage units are e.g. tablets, which can be powdered with grooves promoting the halving or quartering of the tablet in order to exactly administer the required amount of the active ingredient.

Tablets can be coated with an acid-soluble layer in order to assure the release of the active ingredient content after leaving the stomach. Such tablets are enteric-coated. A similar effect can be achieved also by encapsulating the active ingredient.

The pharmaceutical compositions for oral administration can contain e.g. lactose or starch as excipients, sodium carboxymethylcellulose, methylcellulose, polyvinyl pyrrolidine or starch paste as binders or granulating agents. Potato starch or microcrystalline cellulose is added as disintegration agents, but ultraamylopectin or formaldehyde casein can also be used. Talcum, colloidal silicic acid, stearin, calcium or magnesium stearate can be used as antiadhesive and lubricants.

The tablet can be manufactured for example by wet granulation, followed by pressing. The mixed active ingredients and excipients, as well as in given case part of the disintegrants are granulated with an aqueous, alcoholic or aqueous alcoholic solution of the binders in an appropriate equipment, then the granulate is dried. The other disintegrants, lubricants and antiadhesive agents are added to the dried granulate, and the mixture is pressed to a tablet. In given case the tablets are made with halving groove to ease the administration.

The tablets can be made directly from the mixture of the active ingredient and the proper auxiliaries by pressing. In given case, the tablets can be coated by using additives commonly used in the pharmaceutical practice, for example stabilizers, flavoring, coloring agents, such as sugar, cellulose derivatives (methyl- or ethylcellulose, sodium carboxymethylcellulose, etc), polyvinyl pyrrolidone, calcium phosphate, calcium carbonate, food coloring agents, food laces, aroma agents, iron oxide pigments, etc. In the case of capsules the mixture of the active ingredient and the auxiliaries is filled into capsules.

Liquid oral compositions, for example suspensions, syrups, elixirs can be made by using water, glycols, oils, alcohols, coloring and flavoring agents.

For rectal administration the composition is formulated in suppositories or clysters. The suppository can contain beside the active ingredient a carrier, so called adeps pro suppository. Carriers can be vegetable oils, such as hydrogenated vegetable oils, triglycerides of $C_{12}$-$C_{18}$ fatty acids (preferably the carriers under the trade name Witepsol). The active ingredient is homogeneously mixed with the melted adeps pro suppository and the suppositories are moulded.

For parenteral administration the composition is formulated as injection solution. For manufacturing the injection solution the active ingredients are dissolved in distilled water and/or in different organic solvents, such as glycolethers, in given case in the presence of solubilizers, for example polioxyethylensorbitane-monolaurate, -monooleate, or monostearate (Tween 20, Tween 60, Tween 80). The injection solution can also contain different auxiliaries, such as conserving agents, for example ethylendiamine tetraacetate, as well as pH adjusting agents and buffers and in given case local anaesthetic, e.g. lidocain. The injection solution containing the active ingredient of the invention is filtered before it is filled into ampoules, and it is sterilized after filling.

If the active ingredient is hygroscopic, then it can be stabilized by liophylization.

Characterization Method

Compounds of the present invention were characterized by high performance liquid chromatography coupled to mass selective detector (LC/MS) using HP 1100 Binary Gradient chromatography system with Microplate Sampler (Agilent, Waldbronn), controlled by ChemStation software. HP diode array detector was used to acquire UV spectra at 225 and 240 nm. All experiments were performed using HP MSD (Agilent, Waldbronn) single quadruple spectrometer equipped with an electrospray ionization source to determine the structure.

The synthesized products were dissolved in 1 ml of DMSO (Aldrich, Germany). 100 µl of each solution was diluted with DMSO to 1000 µm volume. Analytical chromatographic experiments were performed on Discovery RP C-16 Amide, 5 cm×4.6 nm×5 µm pin column from Supelco (Bellefonte, Pa.) with a flow rate of 1 ml/minute for qualification. The obtained compounds were characterized by their k' value (purity, capacity factor). k' factors are evaluated by the following formula:

$$k'=(t_R-t_0)/t_0$$

where k'=capacity factor, $t_R$=retention time and $t_0$=eluent retention time.

The A eluent was trifluoroacetic acid (TFA) (Sigma, Germany) containing 0.1% water, the B eluent was 95% acetonitrile (Merck, Germany) containing 0.1% TFA and 5% A eluent. Gradient elution was used, starting with 100% A eluent and processing to 100% B eluent over a period of 5 minutes.

The following examples illustrate the invention without the intention of limitation anyway.

EXAMPLE 1

2-(4-Benzylidene-piperidine-1-yl)-2-oxo-N-(2-oxo-2,3-dihydro-benzooxazol-6-yl)-acetamide 1a) 1-Benzyl-4-benzylidene-piperidine Under argon, to a stirred solution of 133.2 g (704 mmol) of N-benzyl-4-piperidone (Aldrich) and 161 g (705 mmol) of benzyl-phosphonic acid diethyl ester (Aldrich) in 1350 ml of dimethylformamide 40.5 g (60%, 37.5 mmol) of sodium hydride is added at 0° C. The reaction mixture is stirred for 2 h at 20° C., 100 ml of ethanol is added drop wise, poured into 1500 ml of water and extracted with diethyl ether. The organic layer is dried over sodium sulfate and concentrated. The crude product is used in the next step. Mp.: oil.

1b) 4-benzylidene-piperidine hydrochloride

To a stirred solution of the previously obtained crude 1-benzyl-4-benzylidene-piperidine (~704 mmol) in 2 l of dichloroethane 80 ml (741 mmol) of 1-chloroethyl-chloroformate is added drop wise at 0° C. The reaction mixture is stirred at 0° C. for 1 h and refluxed for 1 h, then concentrated and the residue is dissolved in 1 l of methanol, refluxed for 1 h. The reaction mixture is concentrated and the residue is crystallized with acetone to yield 103.25 g (70.1%) of the title compound. Mp.: 186° C. (acetone).

1c) (4-benzylidene-piperidine-1-yl-oxo-acetic acid ethyl ester

To a stirred solution of 103.25 g (0.492 mol) of 4-benzylidene-piperidine hydrochloride and 144.55 ml (1.039 mol) of triethylamine in 1 l of chloroform 55.75 ml (0.499 mol) of ethyl oxalyl chloride is added drop wise below 10° C., and the reaction mixture is stirred at room temperature for 1 h. Then 200 ml of water and 200 ml of 8% sodium hydrogen carbonate solution is added to the mixture, the organic layer is separated, dried over sodium sulfate and concentrated. The crude product is used in the next step. Mp.: oil.

1d) (4-benzylidenepiperidine-1-yl)-oxo-acetic acid

To a stirred solution of the previously obtained crude (4-benzylidene-piperidine-1-yl)-oxo-acetic acid ethyl ester (~0.492 mol) in 200 ml of ethanol a solution of 27.6 g (0.69 mol) of sodium hydroxide in 300 ml of water and 500 ml of ethanol is added. The reaction mixture is stirred at room temperature for 1 h then cooled and acidified with hydrochloric acid. The precipitated solid is collected, washed with water to yield 107.32 g (88.9%) of the title compound. Mp.: 125° C. (ethanol-water)

1e) 2-(4-Benzylidene-piperidine-1-yl)-2-oxo-N-(2-oxo-2,3-dihydro-benzooxazol-6-yl)-acetamide A mixture of 49 mg (0.2 mmol) of (4-benzylidene-piperidine-1-yl)-oxo-acetic acid, 33 µl (0.24 mmol) of triethylamine, 30 mg (0.2 mmol) of 6-amino-3H-benzoxazol-2-one [J. Chem. Soc., 321. (1938)] 79.6 mg (0.21 mmol) of HBTU [O-benzotriazol-1-yl-N,N,N',N'-tetramethyluronium hexafluorophosphate (Advanced Chem. Tech.)] and 1 ml of dimethylformamide is stirred at room temperature for 24 h. The reaction mixture is purified by column chromatography using Kieselgel 60 (Merck) as adsorbent and toluene:methanol=4:1 as eluent. The quality and the quantity of the product are determined by HPLC-MS method as described above. k'=9.66.

Using the above described procedure we prepared the following compounds of formula (I):

TABLE 5

(I)

| No. | X/Y–NH– structure | Z | k' |
|---|---|---|---|
| 1 | benzoxazol-2-one (O=, N-H, O ring) -NH- | H | 9.66 |
| 2 | benzimidazol-2-one (O=, N-H, N-H) -NH- | H | 8.694 |

TABLE 5-continued (I)

| No. | Ar (X/Y aniline group) | Z | k' |
|---|---|---|---|
| 3 | 1-methyl-2-oxo-2,3-dihydro-1H-benzimidazol-5-yl(methylamino) | H | 9.29 |
| 4 | 2-oxoindolin-5-yl(methylamino) | H | 8.99 |
| 5 | 2-oxo-2,3-dihydrobenzothiazol-6-yl(methylamino) | H | 10.27 |
| 6 | 2-thioxo-2,3-dihydrobenzoxazol-6-yl(methylamino) | H | 10.66 |
| 7 | 3-oxo-3,4-dihydro-2H-benzo[1,4]oxazin-7-yl(methylamino) | H | 9.78 |
| 8 | 2-oxo-2,3-dihydrobenzoxazol-5-yl(methylamino) | H | 9.73 |
| 9 | 4-acetamidophenyl(methylamino) | H | 9.385 |
| 10 | 4-(methylsulfonamido)phenyl(methylamino) | H | 9.55 |
| 11 | 2-oxo-2,3-dihydrobenzoxazol-6-yl(methylamino) | 4-Cl | 10.73 |
| 12 | 2-oxo-2,3-dihydro-1H-benzimidazol-5-yl(methylamino) | 4-Cl | 10.01 |
| 13 | 1-methyl-2-oxo-2,3-dihydro-1H-benzimidazol-5-yl(methylamino) | 4-Cl | 10.38 |
| 14 | 2-oxoindolin-5-yl(methylamino) | 4-Cl | 10.18 |
| 15 | 2-oxo-2,3-dihydrobenzothiazol-6-yl(methylamino) | 4-Cl | 11.29 |
| 16 | 2-thioxo-2,3-dihydrobenzoxazol-6-yl(methylamino) | 4-Cl | 11.62 |
| 17 | 3-oxo-3,4-dihydro-2H-benzo[1,4]oxazin-7-yl(methylamino) | 4-Cl | 10.766 |
| 18 | 2-oxo-2,3-dihydrobenzoxazol-5-yl(methylamino) | 4-Cl | 10.656 |

TABLE 5-continued
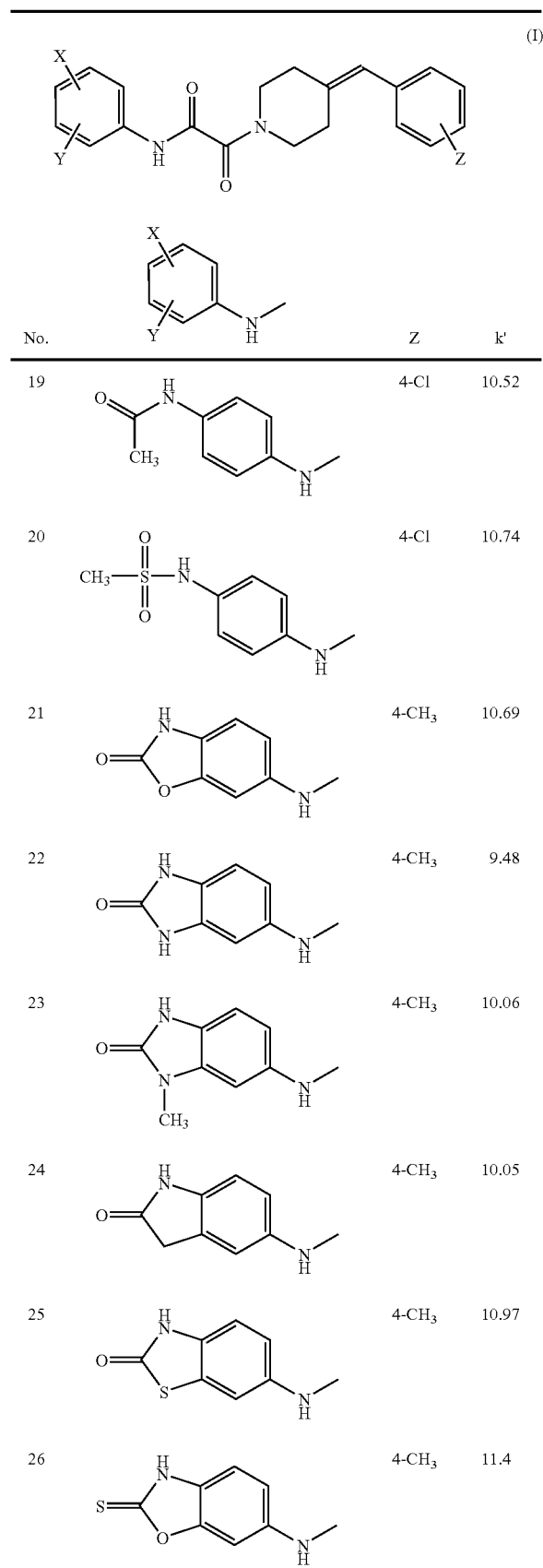
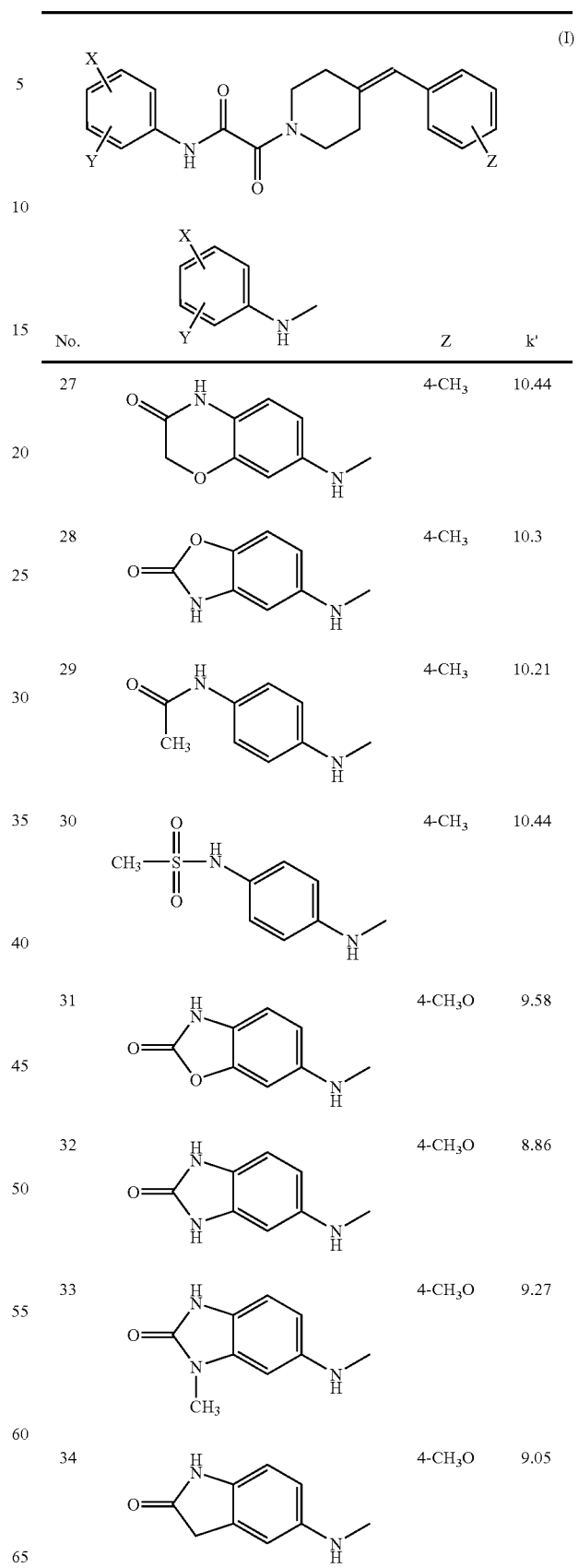

TABLE 5-continued

General formula (I):

X,Y-substituted phenyl-NH-C(O)-C(O)-N(piperidin-4-ylidenemethyl-phenyl-Z)

| No. | Y-aniline substituent (structure) | Z | k' |
|---|---|---|---|
| 35 | 2-oxo-2,3-dihydro-1H-benzimidazol-5-yl-NH- | 4-CH$_3$O | 10.27 |
| 36 | 2-thioxo-2,3-dihydro-1H-benzoxazol-6-yl-NH- | 4-CH$_3$O | 10.73 |
| 37 | 3-oxo-3,4-dihydro-2H-benzo[1,4]oxazin-7-yl-NH- | 4-CH$_3$O | 9.65 |
| 38 | 2-oxo-2,3-dihydro-benzoxazol-6-yl-NH- | 4-CH$_3$O | 9.542 |
| 39 | 4-acetylamino-phenyl-NH- | 4-CH$_3$O | 9.39 |
| 40 | 4-(methanesulfonylamino)-phenyl-NH- | 4-CH$_3$O | 9.64 |
| 41 | 2-oxo-2,3-dihydro-benzoxazol-6-yl-NH- | 4-F | 8.29 |
| 42 | 2-oxo-2,3-dihydro-1H-indol-5-yl-NH- | 4-F | 7.77 |

EXAMPLE 2

Preparation of Pharmaceutical Compositions a) Tablets 0.01-50% of active ingredient of formula (I), 15-50% of lactose, 15-50% of potato starch, 5-15% of polyvinyl pyrrolidone, 1-5% of talc, 0.01-3% of magnesium stearate, 1-3 to of colloid silicon dioxide and 2-7% of ultraamylopectin are mixed, then are granulated by wet granulation and pressed to tablets.

b) Dragées, Filmcoated Tablets

The tablets made according to the method described above are coated by a layer consisting of entero- or gastrosolvent film, or of sugar and talc. The dragées are polished by a mixture of beeswax and carnuba wax.

c) Capsules 0.01-50% of active ingredient of formula (I), 1-5% of sodium lauryl sulfate, 15-50% of starch, 15-50% of lactose, 1-3% of colloid silicon dioxide and 0.01-3% of magnesium stearate are thoroughly mixed, the mixture is passed through a sieve and filled in hard gelatin capsules.

d) Suspensions

Ingredients: 0.01-15% of active ingredient of formula (I), 0.1-2% of sodium hydroxide, 0.1-3% of citric acid, 0.05-0.2% of nipagin (sodium methyl 4-hydroxybenzoate), 0.005-0.02% of nipasol, 0.01-0.5% of carbopol (polyacrylic acid), 0.1-5% of 96% ethanol; 0.1-1% of flavoring agent, 20-70% of sorbitol (70% aqueous solution) and 30-50% of distilled water.

To solution of nipagin and citric acid in 20 ml of distilled water, carbopol is added in small portions under vigorous stirring, and the solution is left to stand for 10-12 h. Then the sodium hydroxide in 1 ml of distilled water, the aqueous solution of sorbitol and finally the ethanolic raspberry flavor are added with stirring. To this carrier the active ingredient is added in small portions and suspended with an immersing homogenizator. Finally the suspension is filled up to the desired final volume with distilled water and the suspension syrup is passed through a colloid milling equipment.

e) Suppositories

For each suppository 0.01-15% of active ingredient of formula (I) and 1-20% of lactose are thoroughly mixed, then 50-95% of adeps pro suppository (for example Witepsol 4) is melted, cooled to 35° C. and the mixture of active ingredient and lactose is mixed in it with homogenizator. The obtained mixture is mould in cooled forms.

f) Lyophilized Powder Ampoule Compositions

A 5% solution of mannitol or lactose is made with bidistilled water for injection use, and the solution is filtered so as to have sterile solution. A 0.01-5% solution of the active ingredient of formula (I) is also made with bidistilled water for injection use, and this solution is filtered so as to have sterile solution. These two solutions are mixed under aseptic conditions, filled in 1 ml portions into ampoules, the content of the ampoules is lyophilized, and the ampoules are sealed under nitrogen. The contents of the ampoules are dissolved in sterile water or 0.9% (physiological) sterile aqueous sodium chloride solution before administration.

What we claim is:

1. New 4-benzylidene-piperidin derivatives of formula (I)

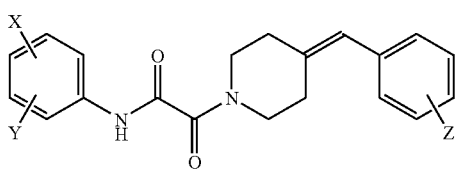

wherein the neighboring X and Y groups together form an optionally substituted ring selected from pyrrolidine, oxo- or thioxo-pyrrolidine; imidazolidine, oxo- or thioxo-imidazolidine, oxazolidine, oxo- or thioxo-oxazolidine and oxo- or thioxo-thiazolidine; Z is hydrogen or halogen atom, nitro, amino, $C_1$-$C_4$ alkyl, $C_1$-$C_4$ alkoxy, cyano, trifluoromethyl, trifluoromethoxy group—and optical antipodes, racemates and salts thereof.

2. A compound of the following group of 4-benzylidene-piperidin derivatives belonging to the scope of claim 1:
  2-(4-benzylidene-piperidin-1-yl)-2-oxo-N-(2-oxo-2,3-dihydro-benzooxazol-6-yl)-acetamide;
  2-(4-benzylidene-piperidin-l-yl)-2-oxo-N-(2-oxo-2,3-dihydr-o-benzothiazol-6-yl)-acetamide,
  2-[4-(4-chloro-benzylidene)-piperidin-1-yl]-2-oxo-N-(2-oxo-2,3-dihydro-benzooxazol-6-y1) -acetamide,
  2-[4-(4-chloro-benzylidene)-piperidin-1-yl]-2-oxo-N-(2-oxo-2,3-dihydro-benzoimidazol-5-yl) -acetamide,
  2-[4-(4-chloro-benzylidene)-piperidin-1-yl]-2-oxo-N-(2-oxo-2,3-dihydro-benzothiazol-6-y1) -acetamide,
  2-[4-(4-methyl-benzylidene)-piperidin-1-yl]-2-oxo-N-(2-oxo-2,3-dihydro-benzoimidazol-5-yl) -acetamide,
  2-[4-(4-methyl-benzylidene)-piperidin-1-yl]-2-oxo-N-(2-oxo-2,3-dihydro-benzothiazol-6-yl) -acetamide,
  2-[4-(4-methoxy-benzylidene)-piperidin-1-yl]-2-oxo-N-(2-oxo-2,3-dihydro-benzoimidazol -5-yl)-acetamide,
  2-[4-(4-methoxy-benzylidene)-piperidin-1-yl]-2-oxo-N-(2-oxo-2,3-dihydro-benzothiazol-6-yl) -acetamide,
  N-(4-methanesulfonylamino-phenyl)-2-[4-(4-methoxy-benzylidene)-piperidin- 1-yl]-2-oxo -acetamide,
  2-[4-(4-fluoro-benzylidene)-piperidin-1-yl]-2-oxo-N-(2-oxo-2,3-dihydro-benzooxazol-6-y1)  -acetamideand optical antipodes, racemates and salts thereof.

3. A pharmaceutical composition comprising an effective amount of the a compound of formula (I)—in claim 1 and pharmaceutically acceptable carriers, excipients, diluents, stabilizers, wetting or emulsifying agents, pH- and osmotic pressure-influencing, flavoring or aromatizing, formulation-promoting or formulation-providing additives.

4. Process for preparing the 4-benzylidene-piperidin derivatives of formula (I) in claim 1 characterized by reacting a secondary amine of formula (II)

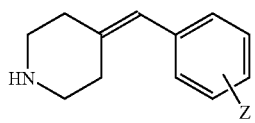

where Z has the same meaning as given for formula (I)— with ethyl oxalylchloride in a suitable solvent in the presence of a base, saponifying the obtained ester compound of formula (III)

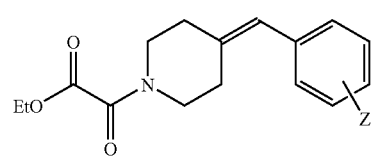

where Z has the same meaning as given for formula (I)— with an alkali hydroxide and reacting the obtained oxalamid acid of formula (IV)

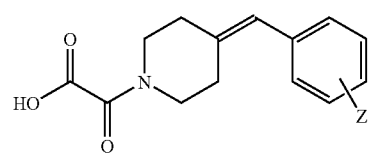

wherein the meaning of Z is as described above for formula (I)—or a reactive derivative of it with an aniline of formula (V)

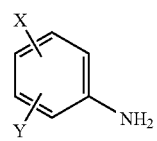

wherein the meaning of X and Y are as given before for formula (I)—in dichloromethane, then transforming optionally the so obtained 4-benzylidene-piperidin derivatives of formula (I)—in claim 1—into other compounds of formula (I) by introducing new substituents and/or modifying or removing the existing ones, and/or by forming salt and/or liberating the compound of formula (I) from salts by known methods.

5. Process as claimed in claim 4, characterized by reacting an active derivative of the carboxylic acid of formula (IV)—wherein the meaning of Z is as given in claim 1—with the aniline of formula (V)—wherein the meaning of X and Y are as given in claim 1—in the presence of a base.

6. Process as claimed in claim 4, characterized by reacting the carboxylic acid of formula (IV)—wherein the meaning of Z is as given in claim 1—with the aniline of formula (V)—wherein the meaning of X and Y are as given in claim 1—in the presence of triethylamine and O-benzotriazol -1-yl-N,N,N',N'-tetramethyluronium hexafluorophosphate (HBTU) in dimethylformamide.

7. Process for manufacturing pharmaceutical compositions having NR2B selective NMDA receptor antagonist effect, characterized by mixing a 4-benzylidene-piperidin derivative of formula (I) in claim 1—or optical antipodes or racemates or the pharmaceutically acceptable salts thereof as active ingredients and auxiliary materials, carriers, excipients, diluents, stabilizers, wetting or emulsifying agents, pH- and osmotic pressure-influencing, flavoring or aromatizing, as well as formulation-promoting or formulation-providing additives.

8. A method of treating a disease, in a mammal or human in need thereof, selected from traumatic injury of brain or spinal cord, human immunodeficiency virus(HIV) related neuronal injury, amyotrophic lateral sclerosis, tolerance and/or dependence to opioid treatment of pain, withdrawal syndromes of alcohol, opioids or cocaine, excitotoxicity evoked by brain hypoxia or ischemia, chronic neurodegeneration in Alzheimer's disease, Parkinson's disease or Huntington's disease, pain, chronic pain, neuropathic pain or cancer related pain, epilepsy, anxiety, depression, migraine, psychosis, muscular spasm, dementia of various origin, degenerative disorders of the retina, glaucoma, asthma, tinnitus, and aminoglycoside antibiotic-induced hearing loss comprising administering an effective amount of a compound of formula (I), or optical antipode or racemate or the pharmaceutically acceptable salt thereof, to said mammal or human.

\* \* \* \* \*

UNITED STATES PATENT AND TRADEMARK OFFICE
CERTIFICATE OF CORRECTION

PATENT NO.         : 8,008,326 B2
APPLICATION NO.    : 11/658789
DATED              : August 30, 2011
INVENTOR(S)        : Istvan Borza It is certified that error appears in the above-identified patent and that said Letters Patent is hereby corrected as shown below:

Column 20, Line 14 (Claim 4), please delete "oxalamid" and insert -- oxalamide --, therefor;

Column 20, Line 54 (Claim 6), please delete "benzotriazol -1-yl" and insert -- benzotriazol-1-yl --, therefor.

Signed and Sealed this
Sixth Day of March, 2012

David J. Kappos
*Director of the United States Patent and Trademark Office*